United States Patent [19]

Kacicz et al.

[11] Patent Number: 4,604,366

[45] Date of Patent: Aug. 5, 1986

[54] LEUCITE PORCELAIN

[75] Inventors: Joseph M. Kacicz; Frank P. Fonvielle, both of York, Pa.

[73] Assignee: Dentsply Research & Development Corp., Milford, Del.

[21] Appl. No.: 591,387

[22] Filed: Mar. 20, 1984

[51] Int. Cl.$^4$ .................. C03C 10/10; C03C 8/22; C03C 8/14; C03C 8/02
[52] U.S. Cl. ................................ 501/6; 501/16; 501/17; 501/21; 501/32; 106/35
[58] Field of Search ............ 106/35; 501/32, 16, 501/17, 6, 21

[56] References Cited

U.S. PATENT DOCUMENTS

| | | | |
|---|---|---|---|
| 3,052,982 | 9/1962 | Weinstein et al. | 433/206 |
| 3,052,983 | 9/1982 | Weinstein | 433/223 |
| 3,400,097 | 9/1968 | Weinstein | 106/35 |
| 3,423,828 | 10/1965 | Halpern et al. | 32/8 |
| 3,464,837 | 10/1964 | McLean et al. | 106/35 |
| 3,615,765 | 10/1968 | Bystrova | 501/21 |
| 3,775,164 | 11/1973 | Smith et al. | 501/32 |
| 4,101,330 | 7/1978 | Burk et al. | 106/35 |
| 4,120,729 | 10/1978 | Smyth et al. | 106/35 |
| 4,337,316 | 6/1982 | Votava | 501/21 |

FOREIGN PATENT DOCUMENTS

| | | | |
|---|---|---|---|
| 53-31716 | 3/1978 | Japan | 433/222 |
| 55-3301 | 1/1980 | Japan | 433/222 |

OTHER PUBLICATIONS

Chemical Abstract 81713g; vol. 81; 1974.
Chemical Abstract 63365m; vol. 82; 1975.

Primary Examiner—Mark L. Bell

[57] ABSTRACT

Porcelain compositions, especially dental porcelain compositions, which contain leucite crystals in controlled amounts in a glassy phase matrix to permit selective adjustment of the thermal coefficient of expansion of the porcelain compositions, including methods of preparing and using same and products derived therefrom.

24 Claims, No Drawings

LEUCITE PORCELAIN

FIELD OF THE INVENTION

This invention relates to leucite-containing porcelain compositions and to methods of preparing the same. More particularly, this invention relates to porcelain compositions, especially dental porcelain compositions, which contain leucite crystals in controlled amounts in a glassy phase matrix to permit selective adjustment of the thermal coefficient of expansion of the porcelain compositions.

Although not limited thereto, the invention has particular applications to a series of distinct dental porcelain powders comprising a glassy phase matrix having a predetermined index of refraction and fusion temperature, and in which there is a dispersed leucite phase to impart to the powder a predetermined thermal coefficient of expansion. The invention also contemplates blends of such leucite-containing porcelain powders, each of which comprises a different amount of leucite so as to exhibit a different thermal coefficient of expansion, and to dental porcelain made from such blends. In a particularly suitable application, the invention also contemplates dental products and their preparation, especially such products having metal substrates secured to a leucite-containing porcelain covering wherein the porcelain exhibits a firing temperature in the range of from about 815° C. to about 1315° C. and a preselected thermal coefficient of expansion ranging from $8 \times 10^{-6}$ to about $20 \times 10^{-6}$ in/in/°C. at 500° C.

BACKGROUND OF THE INVENTION

The use of porcelain compositions in the field of dentistry is well known, as are porcelain compositions themselves and procedures for preparing porcelain compositions. See, for example, U.S. Pat. No. 3,423,828 to Halpern, which discloses a synthetic resin denture base comprising a major portion of porcelain particles; U.S. Pat. No. 3,464,837 to McLean, which discloses a porcelain-containing material that is suitable for use as a dental enamel veneer; and U.S. Pat. No. 3,052,982 to Weinstein, which relates to fused porcelain-to-metal teeth. Similarly, porcelains, including dental porcelains, which contain some quantity of leucite are known. See, for example, 82 Chemical Abstracts 63365m, which relates to leucite glass-ceramic enamel compositions which may be bonded to gold alloy substrates; and U.S. Pat. No. 4,101,330 to Burk, which discloses the preparation of a porcelain or ceramic body from a ceramic raw material consisting essentially of at least about 78.1 percent by weight nepheline syenite, about 3 to 7 percent by weight of pre-formed leucite particles and about 0 to 15.5 percent by weight of at least one modifier selected from the class consisting of oxides and oxide precursors of potassium, sodium, and lithium. The ceramic raw materials are such that when fused to form a fired ceramic body, the resulting body comprises a modified nepheline syenite glassy phase having leucite particles dispersed therein.

Other prior art which relates generally to dental and/or porcelain compositions, some of which may contain leucite crystals, include U.S. Pat. No. 4,120,729 to Smyth, entitled "Novel Low Temperature Maturing Dental Glaze;" 81 Chemical Abstracts 81713g, an abstract entitled "Enamels with High Thermal Expansion Doefficient;" U.S. Pat. No. 4,337,316 to Votava, entitled "Sanitary Ware and Process of Production;" U.S. Pat. No. 3,775,164 to Smith, entitled "Method of Controlling Crystallization of Glass;" and U.S. Pat. No. 3,615,765 to Bystrova, entitled "Glaze for Ceramic Parts and Articles."

Dental porcelains generally may be classified as higher fusing porcelains, i.e., those porcelains fusing above about 1000° C., and lower fusing porcelains, i.e., those porcelains fusing below about 1000° C. The higher fusing porcelains generally exhibit resistance to thermal stress and mechanical shock and to erosion by mouth fluids, and have been fused to metals having a compatible thermal coefficient of expansion, such as the platinum-iridium alloys. The lower fusing porcelains have been used for using to lower melting substrates, such as gold alloys, but there have been problems, at least in part, because of the disparity between the thermal coefficient of expansion of the gold alloys and the lower fusing porcelains.

Attempts have been made to match a given porcelain material to a given dental support metal so as to increase the compatibility between their respective thermal coefficients of expansion. These attempts have included the preparation of specifically formulated and prepared porcelains to be used with dental metals having a specific narrow thermal expansion range. For example, in U.S. Pat. No. 3,052,982 to Weinstein, there is disclosed a technique for preparing porcelain coverings for metal supports, wherein the porcelain is tailored in each case to have a thermal coefficient of expansion which is compatible with that of the metal being used for the support. The porcelains disclosed in this patent are prepared by mixing predetermined amounts of components prepared in part from different feldspars and glasses, the composition and relative amounts of the components being responsible for the physical characteristics of the porcelain products.

While techniques of the above type have been used with some success in the art, they often result in porcelains which have expansion characteristics that vary with firing conditions.

Accordingly, it is an object of the present invention to provide dental porcelain compositions which, when fused, provide a porcelain body having controlled coefficient of thermal expansion.

It is another object of the invention to provide dental porcelain compositions which selectively and readily can be tailored for use with a variety of commercially available metal support materials.

Still another object of the invention is to provide an efficient technique for matching the coefficient of thermal expansion of a dental porcelain composition with that of a metal support structure to which the porcelain composition is to be fused.

Another object of the invention is to provide a dental porcelain material having all the characteristics necessary for advantageously producing an aesthetic dental restorative.

Yet another object of the invention is to provide a unique system of leucite-containing raw materials which can be blended and fused to form a dental porcelain having a preselected coefficient of thermal expansion.

Still another object of the invention is to provide a facile technique for providing a range of porcelain materials, each having a preselected coefficient of thermal expansion and each having a firing temperature on the order of about 700° C. to about 1315° C.

Yet another object is to enable the modification of a naturally occurring potash feldspar or glass of the same composition to form a series of thermal expansion control, leucite-containing frits.

Still another object is to control the coefficient of thermal expansion of a dental porcelain through the use of porcelain-forming raw materials comprised of intentionally graded leucite-containing frits prepared from a feldspar material.

These and other objects and advantages of the present invention are achieved, in a broad sense, by first providing a series of leucite-containing, glass-ceramic frits, each of the series containing a different amount of leucite and thus exhibiting a different coefficient of thermal expansion. The series of glass-ceramic frits can be blended selectively with a matrix glass to control the thermal expansion coefficient of the glass matrix/glass-ceramic blend. The matrix glass in combination with the glass-ceramic frits is selected to govern the firing temperature, glass transition temperature, viscosity, and translucency of the resulting system.

In one aspect of the invention, the glass matrix is comprised of a mixture of two glasses. Preferably, one of the glasses would be a relatively higher melting glass having a fusion range on the order of from about 750° C. to about 845° C., preferably 800° C. to about 830° C., and the other would be a relatively lower melting glass having a fusion range in the range of from about 700° C. to about 825° C., preferably 785° C. to about 815° C. In most cases, the difference in fusion range between the lower melting glass and the higher melting glass is at least about 10°–15° C. The mixture or glasses generally would possess the desired balance between fluidity and stiffness, and surface properties attributable to the two glasses comprising the mixture. The glasses also would be selected such that the refractive index of the fusion product of their mixture would be about the same as that of the leucite-containing glass-ceramic frits, and such that the coefficient of thermal expansion of their fusion products would be in the range of from about $9 \times 10^{-6}$ to about $10 \times 10^{-6}$ in/in/°C. at 400° C. Although a number of glasses satisfy the above selection criteria, suitable examples of matrix glasses are shown in Table 1.

TABLE 1

| Constituents | Higher Melting Matrix Glass Percent by Weight | Lower Melting Matrix Glass Percent by Weight |
| --- | --- | --- |
| $SiO_2$ | 67.0–73.0 | 61.0–66.0 |
| $Al_2O_3$ | 7.2–9.3 | 12.3–14.8 |
| CaO | 0.2–1.0 | 2.3–4.5 |
| $Na_2O$ | 12.5–14.4 | 8.5–10.2 |
| $K_2O$ | 6.2–7.1 | 5.0–5.9 |
| $Sb_2O_3$ | 0.1–0.3 | 0.1–0.35 |
| $Fe_2O_3$ | 0.1 | 0.1 |
| PbO | 0.1 | 0.1 |
| $Li_2O_3$ |  | 1.5–3.5 |
| BaO |  | 0.5–1.0 |
| $B_2O_3$ |  | 0.2–0.6 |
| MgO |  | 0.8–2.0 |

Thus, in one aspect of the invention the relatively higher melting glass matrix material may comprise a frit having a composition consisting essentially of, by weight percent, about 67.0 to 73.0 percent silicon dioxide, 7.2 to 9.3 percent aluminum oxide, 0.2 to 1.0 percent calcium oxide, 12.5 to 14.4 percent sodium monoxide, and 6.2 to 7.1 percent potassium oxide, and 0.1 to 0.3 percent antimony(III) oxide, and the second or relatively lower melting glass matrix material may comprise a frit having a composition consisting essentially of by weight percent, about: 61.0 to 66.0 percent silicon dioxide, 12.3 to 14.8 percent aluminum oxide, 2.3 to 4.5 percent calcium oxide, 8.5 to 10.2 percent sodium monoxide, 5.0 to 5.9 percent potassium oxide, 1.5 to 3.5 percent lithium oxide, 0.5 to 1.0 percent barium oxide, 0.2 to 0.6 percent boric oxide, 0.8 to 2.0 percent magnesium oxide, and 0.1 to 0.35 percent antimony (III) oxide.

Generally speaking, the matrix glasses may be mixed over a fairly wide range of higher to lower melting glass. However, it is normally preferred that the higher to lower melting glass be mixed in a ratio of from about 1:10 to 10:1 with ratios of from about 1:2 to 2:1 being most suitable.

The leucite-containing, glass-ceramic fritted materials which are to be blended with the matrix glass are themselves comprised of a glassy phase matrix in which is dispersed particles of leucite crystals. The series of leucite-containing frits are graded in the sense that each frit contains a different amount of leucite particles and thus a different coefficient of thermal expansion. For example, it is contemplated that a first member of the series might contain 10 percent by weight leucite, that a second member might contain 20 percent by weight leucite, that a third member might contain 40 percent by weight leucite, and so on, with the balance of each member being the glassy phase matrix. It is an important feature of the present invention that the glassy phase matrix can be derived from a feldspathic material which is the same feldspathic material that is used to prepare each member of the series. As used in this specification and claims, the term feldspathic material is meant to describe naturally occurring feldspars as well as glasses and mixtures of oxides having substantially the same chemical composition as such naturally occurring feldspars.

In one embodiment of the invention, the series of leucite-containing, glass-ceramic frits is prepared by doping or adding potassium nitrate, potassium carbonate, potassium silicate, or some other equivalent potassium sorce to a feldspathic material such as a potash feldspar, in separate batches, adding a different amount of potassium nitrate to each separate batch. The potassium nitrate-doped batches are then heated in a furnace at a temperature of from about 1120° C. to about 1650° C. or potentially as high as the equipment will allow for a period up to about eight hours. During this heating period, all of the feldspar melts and leucite crystals begin to precipitate. The leucite particles generally are in the micron size range, for example, on the order of about 2 to 50 microns. The resulting frit is cooled and pulverized to a size on the order of −200 mesh for admixture with the matrix glasses described above.

In another embodiment, a frit is prepared from an undoped potash feldspar using the same procedure outlined above. except that no source of potassium is added to the feldspar. The resulting frit, which may be referred to as a zero-doped frit, may be mixed with the matrix glasses described above.

The composition of a series of leucite-containing, glass-ceramic frits prepared in accordance with the invention may vary over relatively wide limits with respect to the amount of leucite contained therein. However, since all of the members of the series are prepared by doping a feldspathic material in a systematic fashion, the overall composition of the various members of the series will be essentially the same, except for the ratio of leucite to residual glass. In addition, those members of the series having higher percentages of leucite will have correspondingly higher coefficients of thermal expansion. It is this difference in thermal expansion which enables the use of the compositions of this invention to prepare dental porcelains having controlled expansion characteristics. The composition of a series of leucite-containing glass-ceramic frits prepared in accordance with a preferred aspect of the invention is shown in Table 2. Also shown in Table 2 is the stoichiometric composition of leucite and a frit prepared only from a potash feldspar and free from detected leucite. Table 3 illustrates the coefficient of thermal expansion of the frits obtained by doping the potash feldspar shown in Table 2 with 0, 2, 4, 6, 9, and 11 percent by weight potassium nitrate, respectively, based on the total composition. It will be appreciated that other potassium nitrate dopant levels or the use of other potassium sources may be used in accordance with this invention as well. It will be appreciated, also, that feldspathic materials other than a naturally occurring potash feldspar may be used.

TABLE 2

Potassium Nitrate Doped Feldspar Series
All Constituents in % by Weight

| Composition | $SiO_2$ | $Al_2O_3$ | FeO | CaO | $Na_2O$ | $K_2O$ | Other |
| --- | --- | --- | --- | --- | --- | --- | --- |
| Potash feldspar | 64.80 | 18.85 | 0.01 | 0.05 | 3.20 | 12.92 | 0.17 |
| Potash Feldspar + 2% $KNO_3$ | 64.19 | 18.67 | 0.01 | 0.05 | 3.17 | 13.74 | 0.17 |
| Potash Feldspar + 4% $KNO_3$ | 63.57 | 18.50 | 0.01 | 0.05 | 3.14 | 14.57 | 0.16 |
| Potash Feldspar + 6% $KNO_3$ | 62.93 | 18.31 | 0.01 | 0.05 | 3.11 | 15.43 | 0.17 |
| Potash Feldspar + 9% $KNO_3$ | 61.95 | 18.02 | 0.01 | 0.05 | 3.06 | 16.76 | 0.16 |
| Potash Feldspar + 11% $KNO_3$ | 61.25 | 17.84 | 0.01 | 0.04 | 3.02 | 17.67 | 0.16 |
| Stoichiometric Leucite | 55.10 | 23.30 | | | | 21.60 | |

TABLE 3

Frit Thermal Expansion Data
($\times 10^{-6}$ in/in/°C.)

| | TE @ 25° C. | | |
| --- | --- | --- | --- |
| Composition | 400° C. | 500° C. | 600° C. |
| *Potash Feldspar | 15.13 | 15.31 | 15.44 |
| *Potash Feldspar + 2% $KNO_3$ | 14.7 | 15.83 | 15.44 |
| | 14.32 | 15.53 | 14.92 |
| **Potash Feldspar + 4% $KNO_3$ | 16.62 | 18.55 | 17.58 |
| | 16.65 | 18.64 | 18.77 |
| | 16.76 | 18.72 | — |
| *Potash Feldspar + 6% $KNO_3$ | 17.19 | 20.21 | 20.77 |
| **Potash Feldspar + 9% $KNO_3$ | 16.21 | 18.51 | 23.16 |
| **Potash Feldspar + 11% $KNO_3$ | 16.35 | 18.52 | 24.56 |
| | 16.48 | 18.63 | 24.98 |

*Fired in Research Kiln
**Fired in Factory Kiln

In one preferred embodiment, a porcelain material, which is suitable for fusion to a metal substrate, is prepared using a two component glass matrix and two or more, but most preferably two, leucite-containing, glass-ceramic frits to control the thermal expansion. The two component glass matrix, which is comprised of a higher melting glass and a lower melting glass, as described above, is blended into separate batches with the two or more glass-ceramic frits to form a series of master frits containing different amounts of leucite crystals. Each master frit thus would be prepared from the two components of the matrix glass and one of the glass-ceramic frits, including, if desired, a zero-doped frit. The porcelain material would then be made by blending together a mixture of two or more master frits. Accordingly, in the case where two master frits are employed, the resulting porcelain would comprise four components, namely: the two glasses comprising the matrix glass and two leucite-containing, glass-ceramic frits. The selection of the master frits would be made so as to obtain the desired coefficient of thermal expansion in the final porcelain. Generally speaking, the resulting porcelain materials selectively would exhibit a coefficient of thermal expansion of from about 10 to about 19 in/in/°C. at 500° C. This would enable a manufacturing technician to prepare quite readily from a stock of a relatively few master frits porcelain materials that would be suitable for use with any dental alloy.

The master frits may comprise a majority of glass matrix material or a majority of glass-ceramic frit as is desired. However, the amount of glass matrix to glass-ceramic used to prepare the master frits generally is in the range of from about 1:10 to 10:1 by weight, and preferably is in the range of from about 1:2 to 2:1.

In another embodiment, the porcelain material can be prepared simply by blending and then firing a mixture of the two glass components comprising the glass matrix and two or more, but preferably two, glass-ceramic frits of different leucite content. Again, if desired, one of the glass-ceramic frits may be prepared from a zero-doped feldspar or from another suitable potassium-doped or zero-doped feldspathic material. In this embodiment, the amounts of the various components generally would be such that the ratio of higher melting to lower melting glass of the glass matrix would be from about 1:10 to 10:1, preferably from about 1:2 to 2:1; the ratio of the two different glass-ceramic frits would be from about 1:10 to 10:1, preferably from about 1:2 to 2:1; and the ratio of the glass matrix (both glasses combined) to the glass-ceramic frit material (all glass-ceramic frit components combined) would be from about 1:10 to 10:1, preferably from about 1:2 to 2:1. Generally speaking, the glass matrix (both glasses combined) will comprise from about 20 to about 80 percent by weight of the total weight of the various components.

It will be appreciated that the present invention enables the preparation of a wide variety of dental prosthetic devices which require a porcelain veneer to be bonded to a metal support, usually through an opaque layer. These devices which include, for example, fixed or removable bridgework, crowns, and the like can be prepared with relative ease and exceptional reproducibility with respect to matching the coefficient of thermal expansion of the porcelain veneer material with that of the metal support.

DESCRIPTION OF THE PREFERRED EMBODIMENTS

Briefly stated, the porcelain compositions of this invention are prepared from a mixture of a glass matrix material and a glass-ceramic frit material, the latter material containing leucite particles and being used for the purpose of controlling the thermal expansion characteristics of the final porcelain composition. As indicated above, the glass matrix material preferably is prepared from a blend of two glass compositions, one having a higher melting point than the other. The two glass compositions are selected such that the combination of the glass matrix and the selected glass-ceramic frits exhibit the desired firing temperature, glass transition temperature, viscosity, and translucency.

The glass-ceramic frits which are selected for admixture with the glass matrix preferably are prepared by potassium-doping a naturally occurring potash feldspar with potassium nitrate or an equivalent potassium source, and then heating the doped feldspar to a temperature of from about 1120° C. to about 1315° C. The heated mixture is held for a period of from about zero to about eight hours, during which time the feldspar forms a glassy phase in which 2 to 50 micron sized leucite crystals precipitate. The resulting glass-ceramic is then cooled and pulverized. The amount of leucite particles dispersed in the glassy phase of the glass-ceramic frits depends upon the amount of potassium nitrate dopant that is used, and in a preferred embodiment, frits are prepared using dopant levels of about 2, 4, 6, 9, and 11 percent potassium nitrate. Obviously, other dopant levels can be used, and in some cases it may be desirable to use a zero-doped material.

The total amount of glass-ceramic frit that is mixed with the total amount of glass matrix may vary, but generally, the ratio of glass-ceramic to glass matrix is from 10:1 to 1.10, and preferably from 2:1 to 1:2. Likewise, the ratio of the two glasses comprising the glass matrix generally may vary over the range of from about 10:1 to 1:10, and preferably from about 2:1 to 1:2.

The four components of the final porcelain material, i.e., the two glasses of the glass matrix and two glass-ceramic frits having different amounts of leucite, may be blended as such and fired to form the porcelain. However, it is more preferred to form master frits by blending separate batches of glass matrix (containing both the higher and lower melting glasses) and a single glass-ceramic frit. The final porcelain composition is then prepared by mixing two or more master frits which contain different amounts of leucite.

The mixture of the four porcelain components, or the mixture of at least two master frits, may then be used to cover a metal support to form a dental prosthetic device in the usual manner.

The following examples illustrate the porcelain compositions of the present invention, including the glass matrix materials and the glass-ceramic frits from which they are formed. Also illustrated is the use of the porcelain compositions in combination with metal substructures or supports of the type which are used in dental prosthetic devices. The examples are merely illustrative of preferred embodiments of the invention and are not to be deemed as limitative thereof. All percentages and parts are given by weight unless noted otherwise.

EXAMPLE 1

A matrix glass was prepared by mixing 25 parts of glass A and 30 parts of glass B noted in Table 4. The glass A and the glass B were in the form of −200 mesh powder.

TABLE 4

| Component | % by Weight, A | % by Weight, B |
|---|---|---|
| $SiO_2$ | 69.79 | 63.84 |
| $Al_2O_3$ | 9.09 | 13.51 |
| CaO | 0.79 | 2.77 |
| $Na_2O$ | 13.45 | 9.39 |
| $K_2O$ | 6.66 | 5.45 |
| $Sb_2O_3$ | 0.22 | 0.22 |
| $Li_2O$ | | 2.26 |
| BaO | | 0.78 |
| $B_2O_3$ | | 0.31 |
| MgO | | 1.47 |

To the above mixture was added 25 parts of a glass-ceramic frit prepared from the feldspar noted in Table 2 doped with 9 percent potassium nitrate and 20 parts of a glass frit prepared from the same feldspar doped with 4 percent potassium nitrate. The glass-ceramic frits were prepared by firing the doped feldspar to a temperature of about 1230° C. and holding the heated mixture for about three hours until the leucite crystals precipitate, whereafter the mixture was cooled and ground to −200 mesh.

The glass matrix/glass-ceramic mixture was blended to form the desired porcelain product. The fusing point of the final product was about 954° C. and its coefficient of thermal expansion was about $1.2 \times 10^{-6}$ in/in/°C. The porcelain product was fused to the alloys shown in Table 5 by different laboratory technicians during the preparation of a three unit bridge product. Of seventeen products so prepared, sixteen proved to be visually acceptable only one was visually unacceptable. The unacceptable product was prepared with the Olympia ® alloy; three other repetitions with the Olympia ® alloy were acceptable.

TABLE 5

| | | | | Cracks Observed With Unaided Eye | |
|---|---|---|---|---|---|
| Dental Alloy | Product Of | Type of Alloy | Number of Repetitions | Cracks | No Cracks |
| Biobond ® II | Dentsply International | Nickel-Chrome | 2 | 0 | 2 |
| Biobond ® C & B | Dentsply International | Nickel-Chrome | 1 | 0 | 1 |
| Cobond ® | Dentsply International | Cobalt-Chrome | 3 | 0 | 3 |
| Will-Ceram ® W-1 | Williams Gold | Platinum-Silver | 2 | 0 | 2 |
| Option ™ | Ney | Palladium-Copper | 3 | 0 | 3 |
| Olympia ® | Jelenko | Gold-Palladium | 4 | 1* | 3 |
| Athenium ™ | Williams Gold | Palladium- | 2 | 1** | 1 |

TABLE 5-continued

| Dental Alloy | Product Of | Type of Alloy | Number of Repetitions | Cracks Observed With Unaided Eye Cracks | No Cracks |
|---|---|---|---|---|---|
| | | Copper | | | |

*Technique related
**Cracks were not observed on receipt of fused bridge product from the dental laboratory.

EXAMPLE 2

Two master frits containing 55 parts glass matrix and 45 parts of a glass-ceramic frit were prepared. The glass matrix was comprised of 25 parts of glass A (Table 4) and 30 parts of glass B (Table 4). The glass-ceramic frit used to prepare the first master frit was prepared in accordance with Example 1 from the potash feldspar shown in Table 2 doped with 4 percent potassium nitrate. The second glass-ceramic frit was prepared in the same manner from the same feldspar doped with 9 percent potassium nitrate. Both of the master frits contained leucite in a 5 to 10 micron particle size range dispersed in the residual glassy phase. The master frit prepared from the 9 percent potassium nitrate-doped feldspar exhibited a thermal expansion coefficient which was significantly higher than that of the master frit prepared from the 4 percent potassium nitrate-doped feldspar.

A porcelain product was prepared from a mixture of equal parts of the first and second master frits. The porcelain product, which had a fusion temperature of about 955° C. exhibited a coefficient of thermal expansion which was intermediate that of the respective master frits. The porcelain product is suitable for fusing to the alloys indicated in Table 5.

EXAMPLE 3

Example 2 was repeated except that the porcelain material was prepared by firing a mixture comprised of the first and second master frits in a ratio of 3.5:1 instead of 1:1. The thermal coefficient of expansion of the resulting porcelain was about $11.9 \times 10^{-6}$ in/in°C. The porcelain product is suitable for fusing to palladium-gold alloy having a relatively low expansion behavior, such as W-3, a product of Williams Gold having 48.5 percent gold, 39.5 percent palladium, and 10.5 percent indium.

EXAMPLE 4

Example 2 was repeated except that the second master frit was prepared from a glass-ceramic derived from a 2 percent potassium nitrate-doped feldspar instead of a 4 percent doped potassium nitrate feldspar.

A porcelain product was prepared from a 2:1 mixture of the first and second master frits. The porcelain product was compatible to the W-3 gold-palladium alloy noted above.

EXAMPLE 5

Example 2 is repeated except that the first master frit is prepareed from glass-ceramic derived from a 6 percent potassium nitrate-doped feldspar instead of a 9 percent potassium nitrate-doped feldspar.

A porcelain product was prepared from equal parts of the first and second master frits. Upon fusing to Cobond, a cobalt-chrome alloy, the porcelain contained several cracks that were visible by the naked eye.

It is preferred by those skilled in the art that porcelain veneers should be in a state of compression on their outer surface to take full advantage of the best qualities of ceramic systems which are far stronger in compression than in tension. The present invention comprises several glass ceramic frits of different and distinct thermal expansions which are blended in specific predetermined ratios to produce a procelain product of desired thermal expansion. The thermal expansion of the porcelain product may thus be optimized to provide compatibility with the various types of alloys intended for porcelain veneering. For example, to provide compatibility with alloys of regular to relatively high expansion behavior, such as Biobond®II, Cobond®, Will-Ceram® W-1 and Option TM.

The porcelain product comprises two different glass ceramic frits blended to produce a thermal expansion of $12.2 \times 10^{-6}$ in. per in. per °C. Where the product is intended for use with relatively low expansion behavior, alloys such as Olympia®, Will-Ceram®W-3, ratio of high to low expansion frits is altered to produce a porcelain product with a thermal expansion of $11.9 \times 10^{-6}$ in. per in. per ° C.

This invention contemplates the use in dentistry of alloys intended for porcelain veneering which might exhibit thermal expansions either higher or lower than those currently in use.

It is to be understood that the invention is not confined to the particular forms shown, described, and exemplified herein, the same being merely illustrative and that the invention may be carried out in other ways without departing from the spirit and scope thereof as set forth in the accompanying claims.

It is claimed:
1. A porcelain raw material comprising:
   a. a first glass material having a first fusion range at a temperature on the order of from about 750° C. to about 845° C., said first glass material consisting essentially of silicon dioxide, aluminum oxide, sodium monoxide and potassium oxide;
   b. a second glass material having a second fusion range at a temperature that is lower than said first fusion range, said second fusion range being on the order of from about 700° C. to about 825° C., said second glass material consisting essentially of silicon dioxide, aluminum oxide, sodium monoxide and potassium oxide;
   c. a first glass-ceramic material consisting essentially of a first amount of leucite crystals dispersed in a glassy phase matrix, said first glass-ceramic material consisting essentially of silicon dioxide, aluminum oxide, sodium monoxide and potassium oxide;
   d. a second glass-ceramic material consisting essentially of a second larger amount of leucite crystals dispersed in a glassy phase matrix, said second glass-ceramic material having a coefficient of thermal expansion that is higher than that of said first glass-ceramic material and consisting essentially of silicon dioxide, aluminum oxide, iron oxide, sodium monoxide and potassium oxide, the respective amounts silicon dioxide, aluminum oxide, and sodium oxide in said first glass-ceramic material being greater than the amounts thereof in said second glass-ceramic material, and the amount of potassium oxide in said first glass-ceramic material being less than the amount thereof in said second glass-ceramic material;

e. said first and second glass materials comprising from 20 to 80 percent by weight of the total raw material and being present in a ratio of 1:10 to 10:1 of said first glass to said second glass;

f. said first and second glass-ceramic materials being present in a ratio of from 1:10 to 10:1; and g. said first and second glass materials and said first and second glass-ceramic materials and the relative amounts thereof being selected such that, upon fusion, the resulting porcelain exhibits a coefficient of thermal expansion on the order of from about $10 \times 10^{-6}$ in/in/°C. to about $19 \times 10^6$ in/in/°C.

2. The raw material of claim 1, wherein said first glass material is a frit having a composition consisting essentially of, by weight percent, about 67.0 to 73.0 percent silicon dioxide, 7.2 to 9.3 percent aluminum oxide, 0.2 to 1.0 percent calcium oxide, 12.5 to 14.4 percent sodium monoxide, and 6.2 to 7.1 percent potassium oxide, and 0.1 to 0.3 percent antimony(III) oxide and wherein said second glass material is a frit having a composition consisting essentially of, by weight percent, about: 61.0 to 66.0 percent silicon dioxide, 12.3 to 14.8 percent aluminum oxide, 2.3 to 4.5 percent calcium oxide, 8.5 to 10.2 percent sodium monoxide, 5.0 to 5.9 percent potassium oxide, 1.5 to 3.5 percent lithium oxide, 0.5 to 1.0 percent barium oxide, 0.2 to 0.6 percent boric oxide, 0.8 to 2.0 percent magnesium oxide, and 0.1 to 0.35 percent antimony(III) oxide.

3. The raw material of claim 1, wherein said first and said second glass-ceramic materials comprise the fusion product of a potassium-doped feldspar, both of said glass-ceramic materials being prepared from the same feldspar with the level of potassium doping being greater for said second glass-ceramic material than for said first glass-ceramic material.

4. The raw material of claim 3, wherein said feldspar is doped with about 4 percent by weight potassium nitrate prior to fusion for preparing said first glass-ceramic material and with about 9 percent potassium nitrate prior to fusion for preparing said second glass-ceramic material.

5. The raw material of claim 1, wherein said first and second glass-ceramic materials comprise the fusion product of a feldspathic material, wherein at least said second of said first and second glass-ceramic materials comprises the fusion product of a potassium-doped feldspathic material, and wherein the level of potassium doping is greater for said second glass-ceramic material than for said first glass-ceramic material.

6. The raw material of claim 5, wherein said first glass-ceramic material comprises the fusion product of feldspathic material which is free from potassium doping.

7. The raw material of claim 6, wherein said first and second ceramic glass-ceramic materials comprise the fusion product of a naturally occurring feldspar.

8. A porcelain raw material consisting essentially of at least two leucite-containing, glass ceramic frits, each of said frits containing a different concentration of leucite and thus a different coefficient of thermal expansion, and each of said frits having been prepared by mixing a mixture of two glass components and a glass-ceramic component that was prepared by fusing and then pulverizing a potassium-doped feldspar, each of said glass-ceramic components having been prepared from the same feldspar with different levels of potassium doping to form correspondingly different levels of leucite therein, the coefficient of thermal expansion of each of said glass-ceramic frits increasing with increasing leucite levels, each of said two glass components consisting essentially of silicon dioxide, aluminum oxide, sodium monoxide and potassium oxide, and said glass-ceramic component consisting essentially of silicon dioxide, aluminum oxide, sodium monoxide and potassium oxide, the ratio of said glass components to said glass-ceramic component in each glass-ceramic frit being from about 1:10 to about 10:1, said glass components and said glass-ceramic component in each of said glass-cermic frits and the relative amounts thereof and of said frits being selected such that, upon fusion, the resulting porcelain exhibits a coefficient of thermal expansion on the order of from about $10 \times 10^{-6}$ to about $19 \times 10^{31\ 6}$ in/in/°C.

9. The raw material of claim 8, consisting essentially of two leucite-containing, glass-ceramic frits, wherein the first of said two glass components consists essentially of, by weight percent, about: 67.0 to 73.0 percent silicon dioxide, 7.2 to 9.3 percent aluminum oxide, 0.2 to 1.0 percent calcium oxide, 12.5 to 14.4 percent sodium monoxide, and 6.2 to 7.1 percent potassium oxide, 0.1 to 0.3 percent antimony (III) oxide, and wherein the second of said two glass components consists essentially of, by weight percent, about 61.0 to 66.0 percent silicon dioxide, 12.3 to 14.8 percent aluminum oxide, 2.3 to 4.5 percent calcium oxide, 8.5 to 10.2 percent sodium monoxide, 5.0 to 5.9 percent potassium oxide, 1.5 to 3.5 percent lithium oxide, 0.5 to 1.0 percent barium oxide, 0.2 to 0.6 percent boric oxide, 0.8 to 2.0 percent magnesium oxide, and 0.1 to 0.35 percent antimony (III) oxide.

10. A porcelain raw material consisting essentially of at least two leucite-containing glass-ceramic frits, each of said frits having a different coefficient of thermal expansion, each of said frits having been prepared by mixing a mixture of two glass components and a glass-ceramic component that was prepared by fusing and then pulverizing a feldspathic material, at least one of said glass-ceramic components having been prepared from a potassium-doped feldspathic material, the coefficient of thermal expansion of each of said glass-ceramic frits increasing with increasing levels of potassium therein, each of said two glass components consisting essentially of silicon dioxide, aluminum oxide, sodium monoxide and potassium oxide, and each of said glass-ceramic components consisting essentially of silicon dioxide, aluminum oxide, sodium monoxide and potassium oxide, said glass components and said glass-ceramic components in each of said glass-ceramic frits and the relative amounts thereof and of said frits being selected such that, upon fusion, the resulting porcelain exhibits a coefficient of thermal expansion on the order of from about $10 \times 10^{-6}$ to about $19 \times 10^{-6}$ in/in/°C.

11. The raw material of claim 10, consisting essentially of two leucite-containing, glass-ceramic frits, wherein the first of said two glass components consists essentially of, by weight percent, about: 67.0 to 73.0 percent silicon dioxide, 7.2 to 9.3 percent aluminum oxide, 0.2 to 1.0 percent calcium oxide, 12.5 to 14.4 percent sodium monoxide, and 6.2 to 7.1 percent potassium oxide, 0.1 to 0.3 percent antimony (III) oxide, and wherein the second of said two glass components consists essentially of, by weight percent, about 61.0 to 66.0 percent silicon dioxide, 12.3 to 14.8 percent aluminum oxide 2.3 to 4.5 percent calcium oxide, 8.5 to 10.2 percent sodium monoxide, 5.0 to 5.9 percent potassium oxide, 1.5 to 3.5 percent lithium oxide, 0.5 to 1.0 percent barium oxide, 0.2 to 0.6 percent boric oxide, 0.8 to 2.0 percent magnesium oxide, and 0.1 to 0.35 percent antimony (III) oxide.

12. A porcelain-forming raw material consisting essentially of a first glass, a second glass, a first glass-ceramic frit, and a second glass-ceramic frit, said first glass having a fusion range in the range of from about 750° C. to about 845° C. and consisting essentially of silicon dioxide, aluminum oxide, sodium monoxide and potassium oxide, said second glass having a fusion range in the range of from about 700° C. to about 825° C., provided, however, that the melting point of said first glass is always at least about 10° C. to about 15° C. higher than the melting point of said second glass, said second glass consisting essentially of silicon dioxide, aluminum oxide, sodium oxide and potassium oxide, said first and second glasses together comprising from about 20 to about 80 percent by weight of the total composition, said first glass-ceramic frit consisting essentially of silicon dioxide, aluminum oxide, sodium monoxide and potassium oxide and being in the form of a first glassy phase matrix having dispersed therein particles of leucite crystals, said second glass-ceramic frit consisting essentially of silicon dioxide, aluminum oxide, sodium monoxide and potassium oxide and being in the form of a second glassy phase matrix having dispersed therein particles of leucite crystals, said first glass-ceramic frit having a greater amount of leucite crystals than said second glass-ceramic frit, said first and second glass-ceramic frits being substantially the same in all other compositional respects such that the coefficient of thermal expansion of said first glass-ceramic frit is higher than the coefficient of thermal expansion of said second glass-ceramic frit, said first and second glass-ceramic frits being present in a weight ratio of from about 1:10 to 10.1.

13. The raw material of claim 11, wherein at least one of said glass-ceramic components has been prepared from a feldspathic material which is free from potassium doping.

14. A method of preparing a porcelain-forming raw material comprising mixing together:
  a. a first glass material consisting essentially of silicon dioxide, aluminum oxide, sodium monoxide and potassium oxide and, having a fusion range at a first temperature range on the order of from about 750° C. to about 845° C.;
  b. a second glass material consisting essentially of silicon dioxide, aluminum oxide, sodium monoxide and potassium oxide and having a fusion range at a second temperature range that is lower than said first temperature range and on the order of from about 700° C. to about 825° C.;
  c. a first glass-ceramic material consisting essentially of silicon dioxide, aluminum oxide, sodium monoxide and potassium oxide and having a first amount of leucite crystals dispersed in a glassy phase matrix; and
  d. a second glass-ceramic material consisting essentially of silicon dioxide, aluminum oxide, sodium monoxide and potassium oxide and having a second larger amount of leucite crystals dispersed in a glassy phase matrix, said second glass-ceramic material having a coefficient of thermal expansion that is higher than that of said first glass-ceramic material; said first and second glass materials comprising from 20 to 80 percent by weight of the total raw material and being present in a ration of 1:10 to 10:1 of said first glass to said second glass; said first and second glass-ceramic materials being present in a ratio of from 1:10 to 10:1; and said first and second glass materials and said first and second glass-ceramic materials and the relative amounts thereof being selected such that, upon fusion, the resulting porcelain exhibits a coefficient of thermal expansion on the order of from about $10 \times 10^{-6}$ to about $19 \times 10^{-6}$ in/in/°C.

15. A method according to claim 14, wherein said first glass material is a frit having a composition consisting essentially of, by weight percent, about 67.0 to 73.0 percent silicon dioxide, 7.2 to 9.3 percent aluminum oxide, 0.2 to 1.0 percent calcium oxide, 12.5 to 14.4 percent sodium monoxide, and 6.2 to 7.1 percent potassium oxide, and 0.1 to 0.3 percent antimony(III) oxide and wherein said second glass material is a frit having a composition consisting essentially of, by weight percent, about: 61.0 to 66.0 percent silicon dioxide, 12.3 to 14.8 percent aluminum oxide, 2.3 to 4.5 percent calcium oxide, 8.5 to 10.2 percent sodium monoxide, 5.0 to 5.9 percent potassium oxide, 1.5 to 3.5 percent lithium oxide, 0.5 to 1.0 percent barium oxide, 0.2 to 0.6 percent boric oxide, 0.8 to 2.0 percent magnesium oxide, and 0.1 to 0.35 percent antimony(III) oxide.

16. A method according to claim 15, wherein said first and said second glass-ceramic materials comprise the fusion product of a potassium-doped feldspathic material, the level of potassium doping being greater for said second glass-ceramic material than for said first glass-ceramic material.

17. A method according to claim 15, wherein said feldspathic material is doped with about 4 percent by weight potassium nitrate prior to fusion for preparing said first glass-ceramic material and with about 9 percent potassium nitrate prior to fusion for preparing said second glass-ceramic material.

18. A method according to claim 16, wherein said feldspathic material is a naturally occurring feldspar.

19. A method according to claim 18, wherein both of glass-ceramic material are prepared from the same feldspar.

20. A method of forming a porcelain-forming raw material comprising the steps of:
  a. forming a first leucite-containing glass-ceramic frit having a first concentration of leucite crystals by fusing and then pulverizing a first potassium-doped feldspathic material, said first frit consisting essentially of silicon dioxide, aluminum oxide, sodium monoxide and potassium oxide;
  b. forming at least a second leucite-containing, glass-ceramic frit having a second concentration of leucite crystals different from said first concentration by fusing and then pulverizing a second potassium-doped feldspathic material having a different level of potassium doping than said first potassium-doped feldspathic material, said second frit consisting essentially of silicon dioxide, aluminum oxide, sodium monoxide and potassium oxide; and c. blending said first and second leucite-containing, glass-ceramic frits in a ratio of from about 1:10 to about 10:1.

21. The method of claim 20, wherein said feldspathic material is a naturally occurring feldspar.

22. A method of forming a leucite-containing, glass-ceramic frit having a thermal coefficient of expansion on the order of about $10 \times 10^{-6}$ to about $19 \times 10^{-6}$ in./in/°C. and a fusion range of from about 1120° C. to about 1650° C., comprising the steps of: mixing together, fusing, and then comminuting two glass components and a leucite-containing, glass-ceramic component, wherein the first of said glass components consists essentially of silicon dioxide, aluminum oxide, sodium monoxide and potassium oxide and has a first fusion range on the order of from about 750° C. to about 845° C., wherein the second of said glass components consists essentially of silicon dioxide, aluminum oxide, sodium monoxide and potassium oxide and has a second fusion range lower than said first fusion range; and wherein said glass-ceramic component consists essentially of silicon dioxide, aluminum oxide, sodium monoxide and potassium oxide and is obtained by fusing and then comminuting a potassium-doped feldspathic material, the ratio of said glass components to said glass-ceramic component being from about 1:4 to 4:1.

23. The method of claim 22, wherein said feldspathic material is a naturally occurring feldspar.

24. The method of claim 22, wherein said first glass component has a fusion range of from about 750° C. to about 845° C. and consists essentially of, by weight percent, about 67.0 to 73.0 percent silicon dioxide, 7.2 to 9.3 percent aluminum oxide, 0.2 to 1.0 percent calcium oxide, 12.5 to 14.4 percent sodium monoxide, and 6.2 to 7.1 percent potassium oxide, and 0.1 to 0.3 percent antimony(III) oxide; wherein said second glass component has a fusion range of from about 700° C. to about 825° C. and consists essentially of, by weight percent, about: 61.0 to 66.0 percent silicon dioxide, 12.3 to 14.8 percent aluminum oxide, 2.3 to 4.5 percent calcium oxide, 8.5 to 10.2 percent sodium monoxide, 5.0 to 5.9 percent potassium oxide, 1.5 to 3.5 percent lithium oxide, 0.5 to 1.0 percent barium oxide, 0.2 to 0.6 percent boric oxide, 0.8 to 2.0 percent magnesium oxide, and 0.1 to 0.35 percent antimony(III) oxide; and wherein said feldspar is doped with from about 2 percent to about 9 percent potassium nitrate prior to being fused.

* * * * *

UNITED STATES PATENT AND TRADEMARK OFFICE
CERTIFICATE OF CORRECTION

PATENT NO. : 4,604,366
DATED : August 5, 1986
INVENTOR(S) : Kacicz/Fonvielle

It is certified that error appears in the above-identified patent and that said Letters Patent are hereby corrected as shown below:

Col. 4, line 42 delete "sorce" and substitute therefore --source--.

Col. 6, line 6 delete "10 to about 19" and substitute therefore--$10 \times 10^{-6}$ to about $19 \times 10^{-6}$--.

Col. 11, line 21 delete "$10^6$" and substitute therefore-- $10^{-6}$ --.

Signed and Sealed this

Tenth Day of November, 1987

*Attest:*

DONALD J. QUIGG

*Attesting Officer*   *Commissioner of Patents and Trademarks*